United States Patent
Plasson et al.

(10) Patent No.: US 9,288,994 B2
(45) Date of Patent: Mar. 22, 2016

(54) **PROCESS FOR BIOLOGICALLY COMBATING *PSEUDOMONAS***

(71) Applicant: AMOEBA, Lyons (FR)

(72) Inventors: Fabrice Plasson, Lyons (FR); Séléna Bodennec, Les Avenieres (FR)

(73) Assignee: AMOEBA, Lyon (FR)

( * ) Notice: Subject to any disclaimer, the term of this patent is extended or adjusted under 35 U.S.C. 154(b) by 0 days.

(21) Appl. No.: 14/365,237

(22) PCT Filed: Dec. 20, 2012

(86) PCT No.: PCT/EP2012/076451
§ 371 (c)(1),
(2) Date: Jun. 13, 2014

(87) PCT Pub. No.: WO2013/092897
PCT Pub. Date: Jun. 27, 2013

(65) Prior Publication Data
US 2014/0322167 A1    Oct. 30, 2014

(30) Foreign Application Priority Data

Dec. 20, 2011  (FR) ...................................... 11 62098

(51) Int. Cl.
*A01N 63/00*     (2006.01)
*C12R 1/90*      (2006.01)

(52) U.S. Cl.
CPC .. *A01N 63/00* (2013.01); *C12R 1/90* (2013.01)

(58) Field of Classification Search
None
See application file for complete search history.

(56) References Cited

FOREIGN PATENT DOCUMENTS

WO  WO 2008/043969   4/2008
WO  WO 2011/153460   12/2011

OTHER PUBLICATIONS

Michel et al., "Naturliche intrazellulare Infektionen bei Acanthamoeben mit Pseudomonas aeruginosa nach ihrer Isolierung aus einer mikrobiologisch beanstandeten Trinkwasser-Hausinstallation eines Krankenhauses=Acanthamoebae isolated from a highly contaminated drinking water system of a hospital exhibited natural," Zentralblatt Fuer Hygiene Und Umweitmedizin, Stuttgart, DE, vol. 196, No. 6, Jan. 1, 1995, pp. 532-544.
"Research on the Relation of Free-Living Amoebae and its Intracellular Bacterium", cited in the first Office Action issued on Dec. 15, 2015 in corresponding Chinese Patent Application No. 2012800621839.
The first Office Action issued on Dec. 15, 2015 in corresponding Chinese Patent Application No. 2012800621839.

*Primary Examiner* — Renee Claytor
*Assistant Examiner* — David Berke-Schlessel
(74) *Attorney, Agent, or Firm* — Fanelli Haag PLLC

(57) ABSTRACT

The invention relates to a method for controlling the proliferation of *Pseudomonas*, with the exception of the treatment methods applied to the human or animal body, characterized in that it uses protozoa of the *Willaertia magna* species, and also to a disinfecting agent containing such protozoa.

5 Claims, 4 Drawing Sheets

PROCESS FOR BIOLOGICALLY COMBATING *PSEUDOMONAS*

Figure 1:
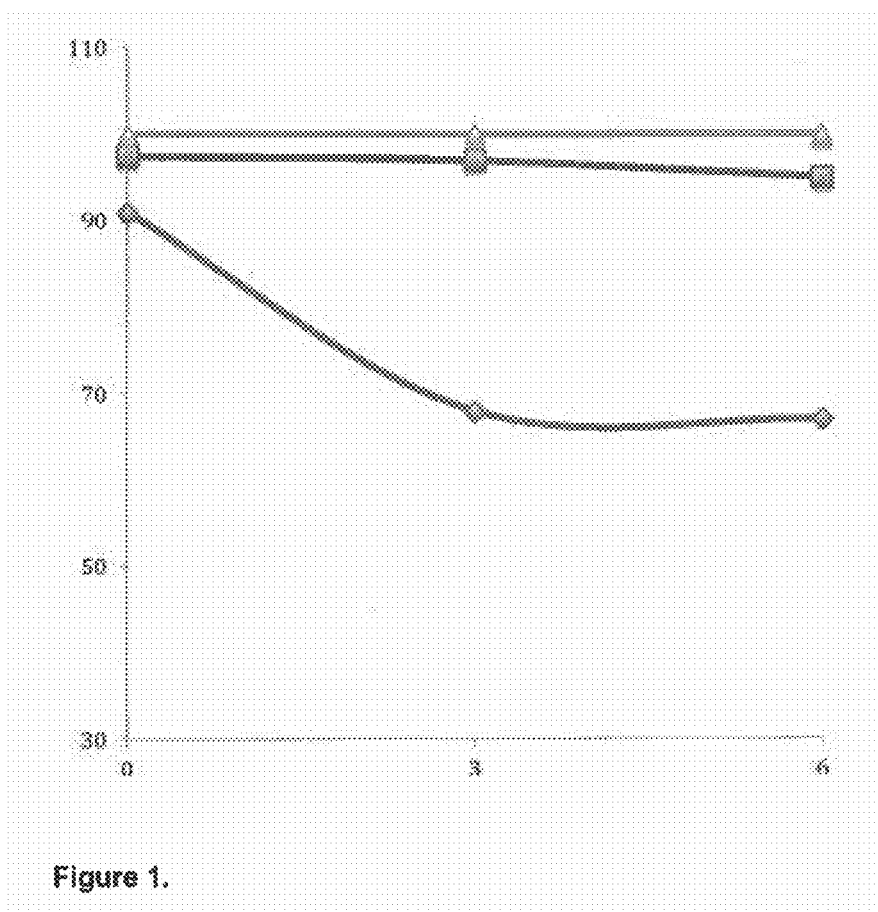

This application is a U.S. National Stage application of PCT International Patent Application No. PCT/EP2012/076451, which was filed on Dec. 20, 2012 which claims priority to French Patent Application No. 1162098 filed Dec. 20, 2011, the disclosure of each of which is incorporated herein by reference in its entirety.

The present invention relates to a novel method for the biological control of the presence of *Pseudomonas*, and the proliferation thereof.

*Pseudomonas* is a Gram-negative bacterium belonging to the family Pseudomonadaceae. In humans, this bacterium is responsible for various skin, visceral and pulmonary infections, in particular cystic fibroses (4, 19). These bacteria are capable of resisting numerous antiseptics and antibiotics (2) (7), which doubtless partly explains their increasingly frequent presence in hospitals, where they can be isolated from the moist environment (sinks, U-bends, vases, towels and washing objects, containers containing water, etc.). Some species also have a pathogenic power toward plants (8), nematodes (10) and amoebae (1, 11, 16). Thus, the monitoring and the control of this bacterium constitute an increasingly important preoccupation.

Generally, it is known that, in the environment, *Pseudomonas* has a ubiquitous distribution (5), since this bacterium has been isolated from the soil, from sewage or from industrial wastewater, and biofilms, characteristics that it shares with free-living amoebae. Several potentially pathogenic bacteria (*Legionella pneumophila, Mycobacterium* spp. and *Escherichia coli* O157:H7) have developed mechanisms for surviving and replicating inside free-living amoebae (15). Furthermore, it has been demonstrated that bacteria, including *Pseudomonas,* can develop various strategies allowing them to evade predation by free-living amoebae (12, 13, 18). In particular, biofilm formation by *Pseudomonas aeruginosa* is one of the mechanisms which allows the bacterium to effectively evade predation by free-living amoebae such as *Acanthamoeba polyphaga* (18). Although it is known that certain free-living amoebae such as *Acanthamoeba* are capable of developing a chemotactic response toward *Pseudomonas* and of feeding on these bacteria (17, 18), it is also been demonstrated that *Pseudomonas aeruginosa* rapidly inhibits the growth of these amoebae and induces their encystment and their death by secreting toxins (11-13, 17, 18). The toxic effect of *Pseudomonas* has also been demonstrated on ciliated protozoa (9).

It therefore clearly appears that free-living protozoa and amoebae constitute an important element of the ecology of *Pseudomonas*. Furthermore, the capacity of *Pseudomonas* to infect and survive intracellularly in protozoa is a powerful indicator that these protozoa are factors which promote the resistance of *Pseudomonas* to the biocidal treatments currently used, as indicated by Michel et al. (14).

In this context, the inventors have demonstrated, totally unexpectedly, that the amoebic genus *Willaertia magna* eradicates *Pseudomonas* bacteria. This biocidal effect is added to by the already demonstrated capacity of *Willaertia magna* for predation toward other amoebic agents that may serve as a vector for *Pseudomonas* (3).

A subject of the present invention is therefore first of all a method for controlling the proliferation of *Pseudomonas*, which uses protozoa of the *Willaertia magna* genus. The methods in accordance with the invention do not include the treatment methods applied to the human or animal body. In the method according to the invention, it is most commonly a gas or liquid stream which is treated with protozoa of the *Willaertia genus* and in particular the *Willaertia magna* species.

The method according to the invention can in particular be used in the disinfection of sanitation water or industrial water distribution networks, cooling circuits for industrial plants, or air-conditioning networks. The protozoa may be directly added to the water or to the liquids circulating in the pipes or networks to be treated. It is also possible to spray them, for example in the form of an aqueous solution as an aerosol, in the industrial networks, chimneys and plants, and on the industrial surfaces, to be disinfected.

Advantageously, the protozoa used in the context of the invention correspond to the strain deposited on Aug. 26, 2006, under number PTA 7824 at the ATCC, or to the strain deposited on Aug. 26, 2006, under number PTA 7825 at the ATCC, these two strains having been deposited in the names of the Centre National de la Recherche Scientifique (CNRS) [French National Center for Scientific Research]—3 rue Michel Ange—75794 Paris Cedex 16/France—and the Uinversité Lyon 1 Claude Bernard [Lyon 1 Claude Bernard University]—43 Boulevard du 11 Novembre 1918—69622 Villeurbanne Cedex/France.

The protozoa belonging to the *Willaertia* genus corresponding to the strain deposited under number PTA 7824 at the ATCC or to the strain deposited under number PTA 7825 at the ATCC are an integral part of the invention. Said deposited strains PTA 7824 and PTA 7825 are also described in the publication of PCT International application WO 2008/043969.

Such protozoa may therefore be used in disinfecting agents, in particular intended for eliminating *Pseudomonas* bacteria and for controlling the proliferation and contamination by *Pseudomonas*.

Furthermore, a subject of the invention is a disinfecting agent containing protozoa of the *Willaertia* genus, and in particular of the *Willaertia magna* species. The protozoa corresponding to the strain deposited under number PTA 7824 at the ATCC or to the strain deposited under number PTA 7825 at the ATCC will be preferred. Advantageously, the disinfecting agent according to the invention is in the form of an aqueous solution or suspension, for example in distilled water. The disinfecting agent may be in a sprayable form, for example as an aerosol or any other means of application.

The *Pseudomonas* proliferation-inhibiting activity of the protozoa of the *Willaertia* genus, and in particular of the *Willaertia magna* species, has been demonstrated by the inventors by comparing the replication of *Pseudomonas* in the *Acanthamoeba* and *Hartmannella* genera used as amoebic models with that observed in the *Willaertia* amoebic genus. The activity of the protozoa of the *Willaertia* genus, and in particular of the *Willaertia magna* species, is also demonstrated by demonstrating the predation effect of *Willaertia magna* on biofilms formed by *Pseudomonas aeruginosas.*

A subject of the invention is also the use of a disinfecting agent or of a protozoan as described above, as a biocide on *Pseudomonas*.

Given the essential role played by amoebae in the proliferation and maintenance of *Pseudomonas* in the external environment, the method and the disinfecting agent according to the invention have numerous advantages, in terms of cost, of effectiveness and of environmental friendliness, in particular.

The examples hereinafter make it possible to illustrate the invention but have no limiting nature.

FIG. 1 shows the spontaneous evolution of the respective populations of *Hartmannella vermiformis* ("square" symbol ■), *Acanthamoeba castellanii* ("diamond" symbol ♦) and *Willaertia* (*Willaertia magna*—"triangle" symbol ▲) amoebae after placing in coculture with *Pseudomonas* at an initial amoeba/bacterium ratio of 10.

The various free-living amoebae are placed in cocultures (time 0 hour=T0) with *Pseudomonas* at a ratio of 10 (10 bacteria/one amoeba) as described in the materials and methods section. Aliquots of the coculture suspensions are taken every 3 hours: i.e. T0, T0+3 h, T0+6 h. The percentage of live amoebae is determined by means of a trypan blue exclusion test and a microscopic observation using a Malassez cell. The data are expressed as % of live cells, negative in the trypan blue exclusion test.

Figure 2:
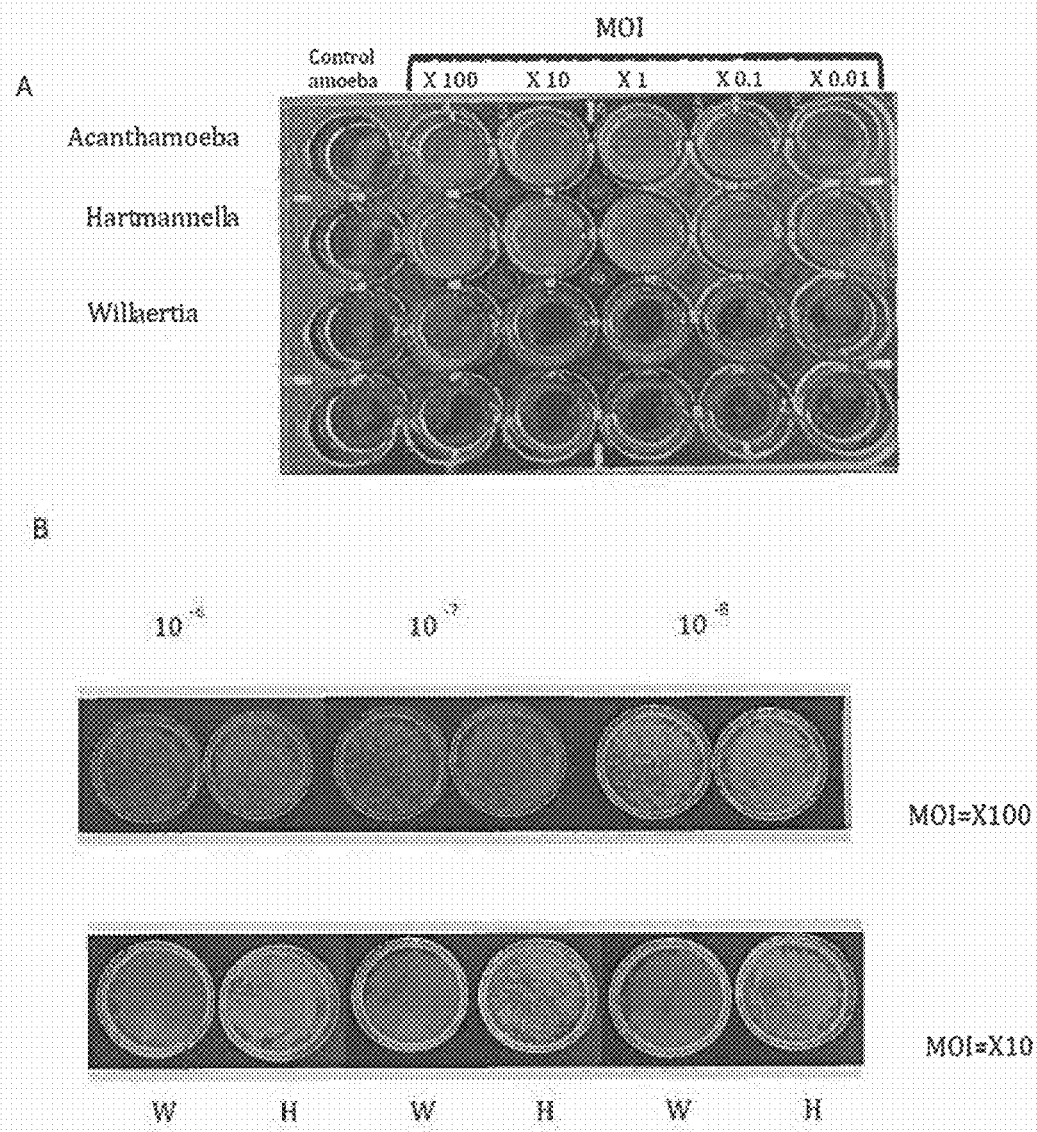

FIG. 2 shows the growth of *Pseudomonas* in cocultures with *Acanthamoeba* and *Hartmannella* but not with *Willaertia*.

The amoebae ($5 \times 10^4$) were suspended in water and inoculated into the wells. After 1 hour, *Pseudomonas* is added to the wells so as to achieve various MOIs as indicated in panel A. The cocultures are incubated at 30° C. and examined after 24 and 48 hours. A. Note the absence of bacterial proliferation in the well containing *Willaertia* with *Pseudomonas*. B. 100 µl of supernatant of the wells containing 100 bacteria/1 amoeba and 10 bacteria/1 amoeba (MOI 100 and MO 10 respectively) are successively diluted (dilutions ranging from $10^{-6}$ to $10^{-8}$ with sterile deionized water) and inoculated onto TSA agar. Note the absence of development of bacterial colonies in the supernatant of the cocultures with *Willaertia magna* (W), and, conversely, the strong development of *Pseudomonas* in the presence of *Hartmanella* (H).

Figure 3:
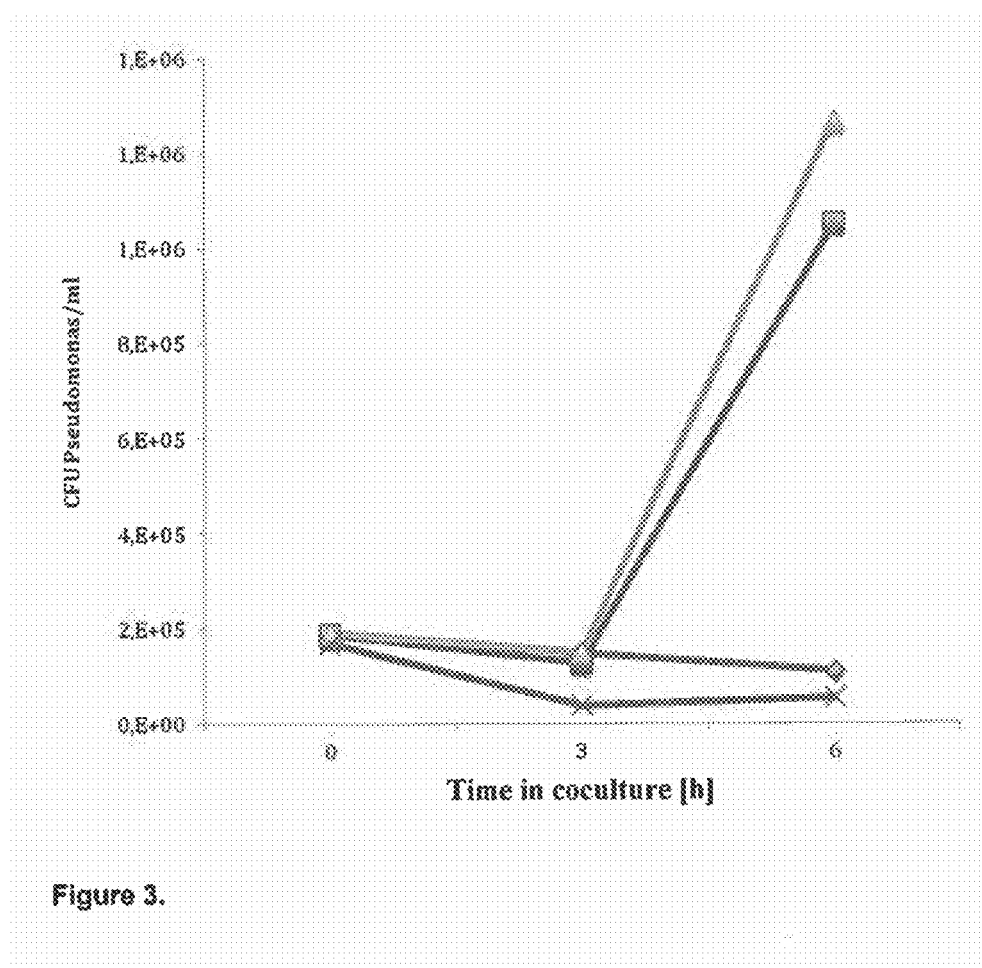

FIG. 3 shows the compared kinetics of the development of *Pseudomonas* ("diamond" symbol ♦), obtained in coculture with various amoebic genera, including the *Willaertia* genus (*Willaertia magna*—"cross" symbol X).

The various free-living amoebae are separately placed in cocultures (time 0 hour=T0) with *Pseudomonas* at a ratio of 10 (10 bacteria/one amoeba). Aliquots of the coculture suspensions are taken every 3 hours: i.e. T0, T0+3 h, T0+6 h, and the *Pseudomonas* concentrations are determined as described in the materials and methods section. A positive control, comprising only the *Pseudomonas* bacteria in a concentration equivalent to that of the cocultures, will serve as a control for the growth of *Pseudomonas* in the medium. Note the bacterial multiplication in the cocultures with *Acanthamoeba castellanii* ("square" symbol ■) and *Hartmannella vermiformis* ("triangle" symbol ▲).

Figure 4:
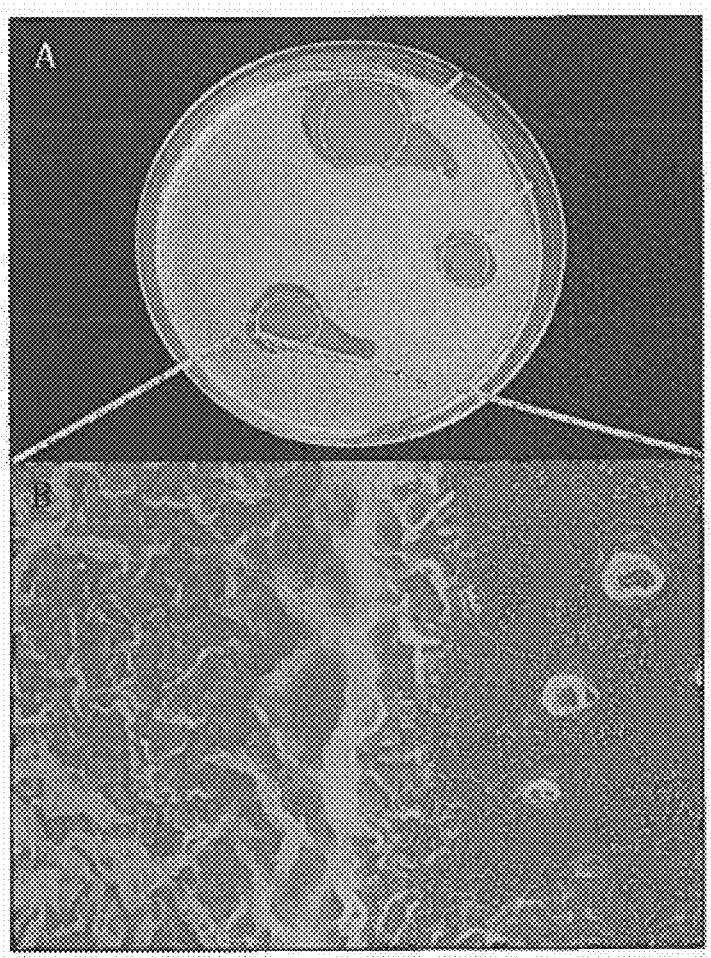

FIG. 4 shows the biocidal effect of *Willaertia magna* on a biofilm formed by *Pseudomonas*.

*Pseudomonas* and *Willaertia magna* were inoculated onto TSA agar, and incubated at 30° C. for 24 h. A. The *Pseudomonas* biofilm lysis plaques form on and beyond the deposits of *Willaertia magna*, as indicated by the arrows on FIG. 4A. B. Front of a biofilm lysis plaque indicated by the arrow. Note, on the right, the site of deposit of *Willaertia magna* in the absence of bacterial film. Note, on the left, the layer of *Pseudomonas*.

1. MATERIALS AND METHODS 1.1. Strains Used:

*Pseudomonas*: the strain used is the CL 5210 strain (Oxoid, France).

It is maintained on TSA (Tryptone Soya Agar) (ref PO 5012, Oxoid, France) at a rate of one subculturing per week. The strain is inoculated in broad streaks onto a TSA plate and incubated for 2 days at 30° C.

Amoebae: the strains used belong to three different amoebic species:

*Hartmannella vermiformis*,

*Acanthamoeba castellanii* (ATCC 30010)

*Willaertia magna* (strains deposited at the ATCC under Nos. PTA7824 and PTA 7825)

These three strains are cultured axenically, in the presence of 10% of fetal calf serum, on SCGYEM medium (Serum Casein Glucose Yeast Extract Medium), distributed into Falcon® tubes (3033) in a proportion of 3 ml per tube. In maintenance, the vegetative forms are subcultured every 8-9 days. For the cocultures, 3-to-4-day subcultures are used so as to have trophozoites right in the exponential growth phase.

The SCGYEM medium is obtained as follows

| | |
|---|---|
| Casein (Merck 1.02244.010) | 10 g |
| $Na_2HPO_4$ | 1.325 g |
| $KH_2PO_4$ | 0.8 g |
| Glucose | 2.5 g |
| Yeast extract (Difco 0127-17-9) | 5 g |
| Distilled water | 900 ml |
| Fetal calf serum | 100 ml |

2.5 ml of NaOH (1N), then $Na_2HPO_4$ and $KH_2PO_4$, are added to 900 ml of distilled water. The mixture is heated slightly on a hotplate, and then the casein is gradually added with magnetic stirring. After the casein has dissolved, the glucose and the yeast extract are incorporated.

After complete dissolution, the mixture is filtered successively on glass fiber (Sartorius SM 6513400), and then on a 1 µm membrane (Whatman 7190 004). The medium is then aliquoted into glass bottles. The bottles are sterilized in an autoclave for 20 minutes at 120° C. Before the definitive use and distribution of the medium, the fetal calf serum is added sterilely, under a laminar flow hood, in a proportion of 10% of the final volume.

1.2. Monoamoebic Coculture of *Pseudomonas*

1.2.1. Preparation of the Bacterial Inoculum:

A suspension of *Pseudomonas* in sterile distilled water is prepared from a 2-day culture on TSA, so as to obtain 1 Optical Density unit at 550 nm, i.e. a concentration of $10^9$ CFU (colony-forming units)/ml.

1.2.2. Carrying Out Monoamoebic Cocultures

The cocultures are carried out in cell culture tubes (Falcon® 3033) containing 3 ml of autoclave-sterilized water. The inoculation of the tubes is carried out in a proportion of $1 \times 10^5$ amoebae/ml, from an axenic amoebic suspension canted beforehand on a Malassez hemocytometer. The infestation of the amoebae with *Pseudomonas* is carried out by fixing a *Pseudomonas*/amoeba ratio of 10, i.e. $1 \times 10^6$ bacteria/ml of incubation medium. Immediately after the infestation, the coculture tubes are centrifuged at low speed (760 g for 10 min) in order to promote contact between amoebae and bacteria. After 10 min, the tubes are resuspended manually and are incubated, in the inclined position, in an incubator at 30° C.

The fates of the amoebae and of *Pseudomonas* placed in coculture are determined in the following way:

The cocultures are monitored for 6 hours after the bacterial infestation. At each time interval (every 3 hours), the coculture tubes are sampled and examined from both the amoebic point of view and the bacterial point of view after vigourous stirring on a vortex in order to detach the amoebae from the walls. For each tube examined:

The amoebae are counted directly on a Malassez cell.

The *Pseudomonas* concentrations are determined by directly plating the culture medium out on TSA after 10-fold serial dilution in sterile distilled water, in Eppendorf microtubes. Each dilution is plated out in triplicate on TSA in a proportion of 100 µl per plate. The plates are then incubated at 30° C. for a minimum of 48 hours. A first reading of the TSAs is carried out 24 hours after the plating out, by counting the colonies; it is followed by a second reading on the 2nd day for confirmation. The *Pseudomonas* concentrations are expressed in CFU/ml of incubation medium, taking into account the dilution factor and assuming that each colony corresponds to one bacterium initially present in the diluted suspension.

For each amoebic genus, the *Pseudomonas* growth curves are represented as a function of time.

In addition, the possible cytotoxic effect of *Pseudomonas* on the various amoebic species is determined in the following way:

by counting the proportion of amoebae which are positive in the trypan blue exclusion test. This test is carried out under a microscope by counting, in a Malassez cell, the number of trypan blue-positive cells/number of total cells.

1.3. Effect of *Willaertia Magna* on *Pseudomonas* Biofilms

The *Willaertia* were deposited on the layer of *Pseudomonas* which had just been plated out on the TSA. The agars are placed at 30° C. for 24 hours so as to allow the development of a bacterial film on the surface of the agar. The agars are then observed under an optical microscope (magnification×400) in order to detect therein the formation of possible bacterial layer lysis plaques.

2. RESULTS 2.1. *Willaertia Magna* Exhibits Resistance to *Pseudomonas*

The effect of *Pseudomonas* on the survival of the various amoebic species tested was determined by means of a trypan blue exclusion test. Very rapidly, after placing *Acanthamoeba castellanii* in coculture with the bacterium, a major cytotoxic effect occurs in this amoebic species, with a drop of ~30% in the viability after 3 hours of coculture (see FIG. 1). Conversely, this phenomenon is never observed when *Willaertia Magna* is placed in coculture with *Pseudomonas*, including up to 9 hours of incubation with a viability which is maintained close to 100% (FIG. 1). Like *Willaertia magna*, the free-living *Hartmanella vermiformis* amoeba does not exhibit any drop in terms of viability determined by trypan blue exclusion (FIG. 1). All of these observations (no encystment and no cytotoxicity induced by *Pseudomonas*) clearly demonstrate that *Willaertia magna* and *Hartmanella vermiformis*, contrary to the other amoebic species of the *Acanthamoeba castellanii* type, exhibit the initial ability to resist *Pseudomonas*.

2.2 Predation of *Pseudomonas* by *Willaertia Magna*

The results of the *Pseudomonas* cocultures carried out in the presence of amoebae belonging to the *Hartmannella* and *Acanthamoeba* genera demonstrate a considerable multiplication of the bacterium in the presence of these two amoebic genera since an increase in the bacterial concentrations is noted in 6 hours (see FIG. 2). Conversely (although the cocultures are carried out under strictly identical conditions), a reduction of about one log in the detectable *Pseudomonas* concentrations is noted in the presence of the *Willaertia magna* amoeba, compared with the control containing only *Pseudomonas* (see FIG. 2 and FIG. 3). The measured drop in the *Pseudomonas* concentrations demonstrates a massive predation effect of *Willaertia magna* toward *Pseudomonas*.

*Willaertia magna* and *Hartmannella vermiformis* survive, but only *Willaertia magna* prevents bacterial proliferation. This effect of *Willaertia magna* on *Pseudomonas* is further illustrated in FIGS. 3 and 4. After incubation for 48 hours in water, the cocultures of *Acanthamoeba* and *Hartmannella* with the bacterium demonstrate a proliferation of *Pseudomonas* (note the cloudy appearance of the wells containing *Pseudomonas* and *Hartmannella* or *Acanthamoeba*, due to bacterial proliferation) (FIG. 3, panel A). The *Pseudomonas* concentrations determined in the supernatant of the coculture wells demonstrate the absence of bacteria with *Willaertia magna* (FIG. 3, panel B) when said bacteria were incubated at an MOI of 10 (10 bacteria/one amoeba).

The predation effect of *Willaertia magna* on *Pseudomonas* is also demonstrated in FIG. 4. Indeed, after 24 hours in the presence of *Willaertia magna*, surfaces of the agar where the bacterial layer has disappeared appear very clearly (these zones are referred to here as bacterial layer/biofilm lysis plaques—FIG. 4, panel A). The microscopic examination of the agars also shows that the *Willaertia magna* are concentrated at the limit of this lysis plaque; this effect is also illustrated in FIG. 4, panel B, where the disappearance of the bacterial layer under the action of the *Willaertia magna* is clearly apparent. All of these data and observations clearly show the predation effect of *Willaertia magna* toward the pathogenic bacterium *Pseudomonas* having developed a biofilm.

LITERATURE REFERENCES

1. Abd H, Wretlind B, Saeed A, Idsund E, Hultenby K, and Sandstrom G. *Pseudomonas aeruginosa* utilises its type III secretion system to kill the free-living amoeba *Acanthamoeba castellanii*. *J Eukaryot Microbiol* 55:-243.2008.
2. Ashish A, Shaw M, Winstanley C, Ledson M J, and Walshaw M J. Increasing resistance of the Liverpool Epidemic Strain (LES) of *Pseudomonas aeruginosa* (Psa) to antibiotics in cystic fibrosis (CF)-A cause for concern? of *J Cyst Fibros* 2011.
3. Bodennec J, Dey R, and Pernin P. Novel method for biologically combating the proliferation of *Legionella pneumophila*, and novel disinfecting agent containing amoebic protozoa of the *Willaertia* genus. edited by University CBL. France: 2010.
4. Bodey G P, Bolivar R, Fainstein V, and Jadeja L. Infections caused by *Pseudomonas aeruginosa*. *Rev Infect Dis* 5:-313.1983.
5. Bredenbruch F, Geffers R, Nimtz M, Buer J, and Haussler S. The *Pseudomonas aeruginosa* quinolone signal (PQS) has an iron-chelating activity. *Environ Microbiol* 8:-1329.2006.
6. Davies B, Chattings L S, and Edwards S W. Superoxide generation during phagocytosis by *Acanthamoeba castellanii:* similarities to the respiratory burst of immune phagocytes. *J Gen Microbiol* 137:-710.1991.
7. Fernandez M, Conde S, de la Torre J, Molina-Santiago C, Ramos J L, and Duque E. Mechanisms of resistance to chloramphenicol by *Pseudomonas putida* KT2440. *Antimicrob Agents Chemother* 2011.
8. Fones H, and Preston G M. Reactive oxygen and oxydative stress tolerance in plant pathogenic *pseudomonas*. *FEMS Microbiol Lett* doi: 10.1111/j.1574-6968.2011,02449.x. [Epub ahead of print]: 2011.

9. Hahn M W, Moore E R, and Hofle M G. Role of Microcolony Formation in the Protistan Grazing Defense of the Aquatic Bacterium *Pseudomonas* sp. MWH1. *Microb Ecol* 39: 175-185, 2000.
10. Irazoqui J E, Troemel E R, Feinbaum R L, Luhachack L G, Cezairliyan B O, and Ausubel F M. Distinct pathogenesis and host responses during infection of *C. elegans* by *P. aeruginosa* and *S. aureus*. *PloS Pathog* 6: e1000982, 2010.
11. Julia A G, and Morgan B M. The effects of selected strains of pigmented microorganisms on small free-living amoeba. *Can J Microbiol* 10:-584.1964.
12. Matz C, Bergfeld T, Rice S A, and Kjelleberg S. Microcolonies, quorum sensing and cytotoxicity determine the survival of *Pseudomonas aeruginosa* biofilms exposed to protozoan grazing. *Environ Microbiol* 6:-226.2004.
13. Matz C, Moreno A M, Alhede M, Mansfield M, Hauser A R, Givskov M, and Kjelleberg S. *Pseudomonas aeruginosa* uses type III secretion system to kill biofilm-associated amoebae. *Isme J* 2: 843-852.2008.
14. Michel R, Burghardt H, and Bergmann H. *Acanthamoeba*, naturally intracellularly infected with *pseudomonas aeruginosa*, after their isolation from a microbiologically contaminated drinking water system in a hospital. *Zentralbi Hyg Umweltmed* 196:-544.1995.
15. Molmeret M, Horn M, Wagner M, Santic M, and Abu Kwaik Y. Amoebae as training grounds for intracellular bacterial pathogens. *Appl Environ Microbiol* 71: 20-28, 2005.
16. Qureshi M N, Perez A A, 2nd, Madayag R M, and Bottone E J. Inhibition of *Acanthamoeba* species by *Pseudomonas aeruginosa*: rationale for their selective exclusion in corneal ulcers and contact lens care systems. *J Clin Microbiol* 31:-1910.1993.
17. Wang X, and Ahearn D G. Effect of bacteria on survival and growth of *Acanthamoeba castellanii*. *Curr Microbiol* 34: 212-215, 1997.
18. Weitere M, Bergfeld T, Rice S A, Matz C, and Kjelleberg S, Grazing resistance of *Pseudomonas aeruginosa* biofilms depends on type of protective mechanism, developmental stage and protozoan feeding mode. *Environ Microbiol* 7:-1601,2005.
19. Yang L, Jelsbak L, and Molin S. Microbial ecology and adaptation in cystic fibrosis airways. *Environ Microbiol* 13: 1682-1689.2011.

The invention claimed is:

1. A method for controlling the proliferation of *Pseudomonas*, with the exception of the treatment methods applied to the human or animal body, comprising contacting a gas or liquid stream or a solid surface with an amoebic protozoa of the species *Willaertia magna* corresponding to the strain deposited under number PTA-7824 at the ATCC or the strain deposited under the number PTA-7825 at the ATCC.

2. The method as claimed in claim 1, characterized in that it is implemented for the disinfection of sanitation water or industrial water distribution networks, cooling circuits for industrial plants, air-conditioning networks, or industrial surfaces.

3. The method as claimed in claim 1, characterized in that it is implemented for controlling the formation of biofilms in water pipes, or surfaces possibly in contact with human or animal food products.

4. A method for eliminating *Pseudomonas* in water or liquids circulating in the pipes or networks to be treated, comprising adding a protozoa corresponding to the strain deposited under number PTA 7824 at the ATCC or to the strain deposited under number PTA 7825 at the ATCC, to said water or liquids.

5. The method as claimed in claim 4, characterized in that said protozoa is in the form of an aqueous solution or suspension.

* * * * *